US00PP25789P3

(12) United States Plant Patent
Zuikevich

(10) Patent No.: US PP25,789 P3
(45) Date of Patent: Aug. 4, 2015

(54) ***BRUNNERA* PLANT NAMED 'ALEXANDER'S GREAT'**

(50) Latin Name: *Brunnera macrophylla*
Varietal Denomination: Alexander's Great

(71) Applicant: Alexander Zuikevich, Minsk (BY)

(72) Inventor: Alexander Zuikevich, Minsk (BY)

( * ) Notice: Subject to any disclaimer, the term of this patent is extended or adjusted under 35 U.S.C. 154(b) by 102 days.

(21) Appl. No.: 13/998,725

(22) Filed: Nov. 26, 2013

(65) Prior Publication Data

US 2015/0150174 P1 May 28, 2015

(51) Int. Cl.
*A01H 5/00* (2006.01)

(52) U.S. Cl.
USPC ..... Plt./412

(58) Field of Classification Search
USPC ..... Plt./412
See application file for complete search history.

*Primary Examiner* — Susan McCormick Ewoldt
(74) *Attorney, Agent, or Firm* — Klarquist Sparkman, LLP

(57) ABSTRACT

A new and distinct form of *Brunnera macrophylla*, with excellent white veiling on the leaves, and extremely large leaf and plant size, and excellent vigor.

3 Drawing Sheets

Botanical denomination: *Brunnera macrophylla.*
Variety designation: 'Alexander's Great'.

BACKGROUND OF THE INVENTION

The present invention relates to a new and distinct cultivar of *Brunnera macrophylla*, given the name, 'Alexander's Great'. *Brunnera* is in the family Boraginaceae. This new cultivar was found in a private garden in Minsk, Belarus. Other *Brunnera macrophylla* were in the area. The exact parents are unknown.

This plant is unique in its combination of intense silver veiling of the leaves and the very large leaf and plant size. Compared to *Brunnera* 'Jack Frost' (U.S. Plant Pat. No. 13,859), the new cultivar is more vigorous, a larger plant, and has longer, much larger leaves.

Compared to *Brunnera* 'Sea Heart' (U.S. Plant Pat. No. 24,684) and 'Silver Heart' (U.S. Plant Pat. No. 24,685), the new variety is more vigorous, with longer, larger leaves, and has a larger habit.

The new variety has been reproduced only by asexual propagation (division and micropropagation). Each of the progeny exhibits identical characteristics to the original plant. Asexual propagation by division and micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
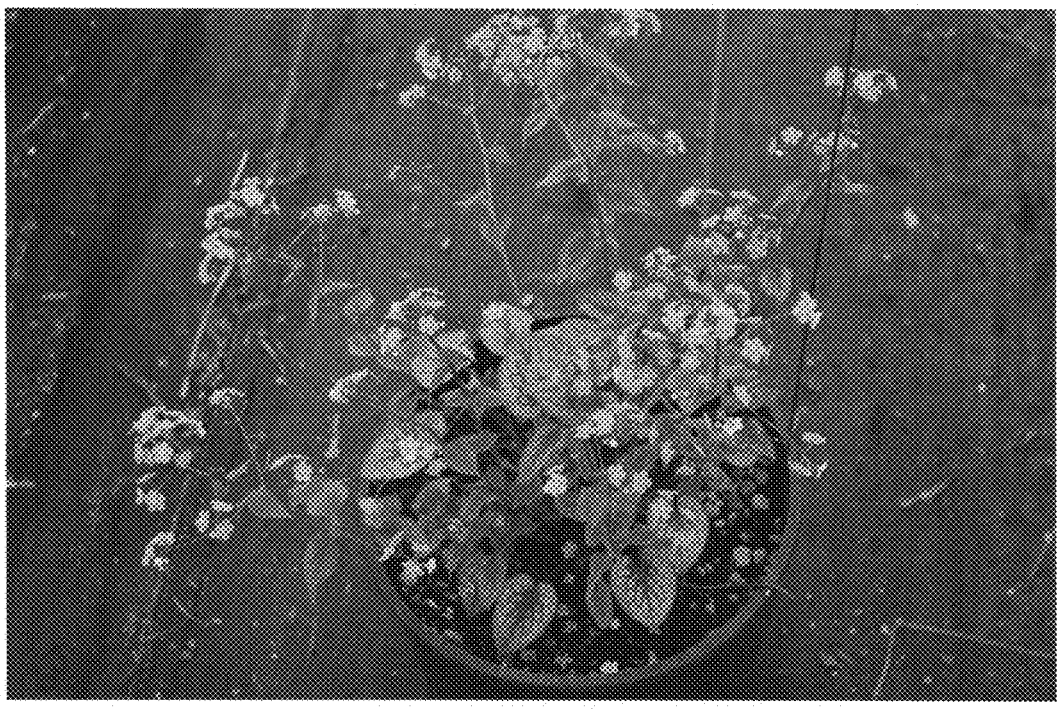
FIG. 1 shows a one-year-old *Brunnera* 'Alexander's Great' growing in a one gallon container in flower in the spring in Canby, Oreg.
Figure 2:
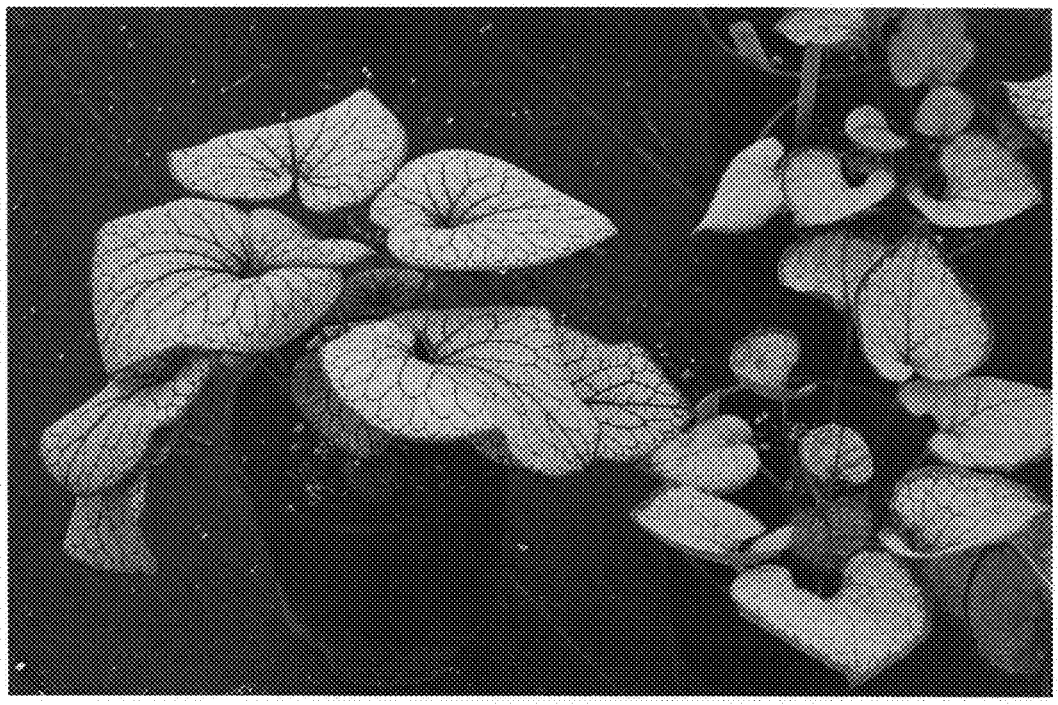
FIG. 2 shows a comparison of 6 month old *Brunnera* 'Alexander's Great' on the left and *Brunnera* 'Jack Frost' (two plants) on the right.
Figure 3:
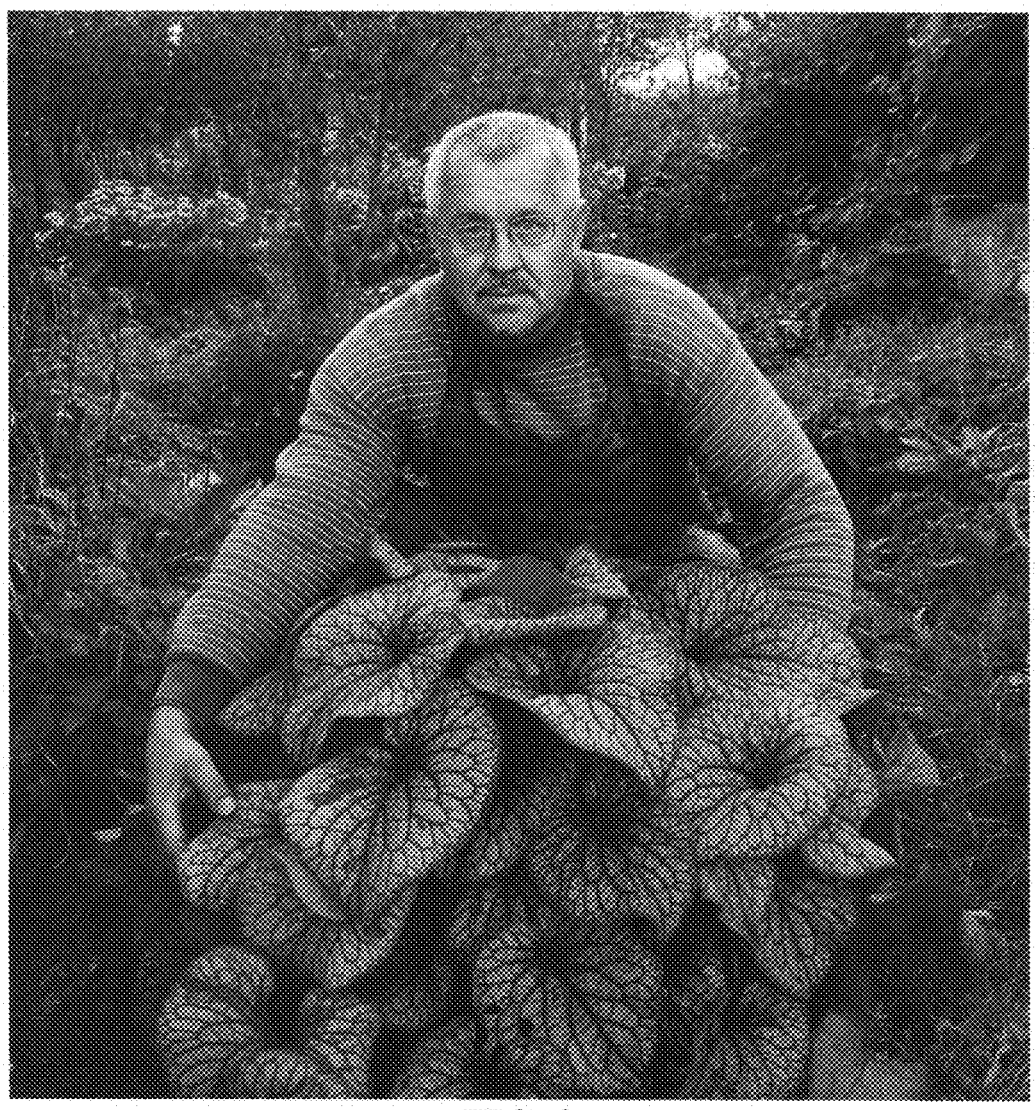
FIG. 3 shows a mature plant of *Brunnera* 'Alexander's Great' with the inventor.

The following is a detailed description of the new *Brunnera* cultivar based on observations of a one-year-old specimen in flower grown in an unheated shade house and a 6 month old plant in leaf grown in a cool greenhouse in Canby, Oreg. The data for the flowers are from the first plant and the data for the plant and leaves are from the second plant. The color descriptions are all based on *The Royal Horticultural Society Colour Chart,* 5$^{th}$ edition.

Plant:
- *Form.*—Rhizomatous, herbaceous perennial.
- *Cold hardiness.*—USDA Zone 3-8.
- *Size.*—Grows to 38 cm wide and 16 cm high.
- *Stem.*—Rosette.
- *Vigor.*—Excellent.

Leaf:
- *Type.*—Simple.
- *Arrangement.*—Basal.
- *Shape.*—Cordate to ovate.
- *Venation.*—Pinnate.
- *Margins.*—Entire.
- *Apex.*—Acute.
- *Base.*—Cordate.
- *Blade size.*—Grows to 17 cm long and 14 cm wide.
- *Surface texture.*—Coarsely pubescent on both sides.
- *Petiole description.*—Grows to 13.5 cm long and 2 mm wide, coarsely pubescent, Yellow Green 147A at base lighting to 147B near blade.
- *Leaf color.*—Topside Greyed Green 192D except for veins and margins Green 139A, bottom side between Green 137B and Yellow Green 147B.

Inflorescence:
- *Type.*—Terminal panicle.
- *Number of flowers.*—100 per panicle.
- *Peduncle.*—21 cm tall and 2 mm wide, pubescent, Yellow Green 145A, with about 9 small petiolate to sessile leaves, grows to 32 mm long and 2.1 mm wide, ovate, entire, acute, attenuate, pubescent with leaf color the same as above.

*Pedicel.*—3 mm long, less than 1 mm wide, pubescent, Yellow Green 145A.

*Bloom period.*—May to June in Canby, Oreg.

Flower bud:

*Size.*—1.3 mm wide and 1.4 mm deep.

*Description.*—Orbicular.

*Surface texture.*—Glabrous.

*Color.*—Purple 76A.

Flower:

*Type.*—Regular.

*Shape.*—Rotate.

*Corolla description.*—5 cm wide and 2 mm deep, top side colored Violet Blue 98A with a White 155D eye, bottom side Violet Blue 97A to 97B; with 5 broadly obovate lobes, each 2 mm wide and 2 mm deep, obtuse, entire, glabrous; tube 1 mm long and 1 to 2 mm wide, outside Purple 77B near lobes to Yellow White 158D.

*Calyx description.*—Campanulate, 1 mm wide and 1 mm deep, 5-lobed, lobes ovate, acute, entire, pubescent outside, glabrous inside.

*Pistil description.*—1, 1 mm long, Yellow Green 144A, ovary 4 lobed and about 0.5 mm long, style and stigma 0.5 mm long.

*Stamen description.*—5, filaments 1 mm long and White 155D, anthers 1 mm long and Black 202A, pollen White 155A.

*Fragrance.*—None.

*Lastingness.*—A spike blooms for about 3 weeks on the plant.

Seed: Nutlets, round, less than 1 mm in size, Brown 200A.

Pests and diseases: *Brunnera* have no major pests or disease problems. This plant has shown no special disease or pest resistance in Canby, Oreg.

I claim:

1. A new and distinct form of *Brunnera* plant substantially as shown and described.

* * * * *